(12) United States Patent
Sedlmair

(10) Patent No.: US 9,778,691 B2
(45) Date of Patent: Oct. 3, 2017

(54) MEDICAL FACILITY

(71) Applicant: Siemens Aktiengesellschaft, Munich (DE)

(72) Inventor: Martin Sedlmair, Zirndorf (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 90 days.

(21) Appl. No.: 14/566,783

(22) Filed: Dec. 11, 2014

(65) Prior Publication Data

US 2015/0169001 A1 Jun. 18, 2015

(30) Foreign Application Priority Data

Dec. 18, 2013 (DE) .................. 10 2013 226 342

(51) Int. Cl.
*G06F 1/16* (2006.01)
*G06F 1/26* (2006.01)
*G06F 3/023* (2006.01)
*G06F 19/00* (2011.01)

(52) U.S. Cl.
CPC .......... *G06F 1/1632* (2013.01); *G06F 1/1698* (2013.01); *G06F 1/266* (2013.01); *G06F 3/0231* (2013.01); *G06F 19/3406* (2013.01)

(58) Field of Classification Search
CPC .......................... G06F 19/3406; G06F 1/1632
See application file for complete search history.

(56) References Cited

U.S. PATENT DOCUMENTS

| 6,035,228 | A   | * | 3/2000 | Yanof   | A61B 19/201 600/429 |
| 7,065,658 | B1  | * | 6/2006 | Baraban | G06F 1/1626 320/108 |
| 2004/0181142 | A1 | * | 9/2004 | Shinno  | A61B 6/00 600/407 |
| 2006/0074286 | A1 | * | 4/2006 | Miller  | A61B 6/032 600/407 |
| 2006/0126290 | A1 | * | 6/2006 | Park    | G06F 1/1632 361/679.41 |
| 2006/0187192 | A1 |   | 8/2006 | Kagermeier et al. | |

(Continued)

FOREIGN PATENT DOCUMENTS

| CN | 101460095 A | 6/2009 |
| CN | 102247152 A | 11/2011 |

(Continued)

OTHER PUBLICATIONS

Office Action for Chinese Patent Application No. 201410785597.5 issued on Dec. 5, 2016 and English translation thereof.

(Continued)

*Primary Examiner* — David M Sinclair
*Assistant Examiner* — Theron S Milliser
(74) *Attorney, Agent, or Firm* — Harness, Dickey & Pierce, P.L.C.

(57) ABSTRACT

A medical facility includes an imaging medical device and at least one portable control/display unit. The imaging medical device includes a number of docking stations, each with a closed surface and designed to establish a wireless data link to the control/display unit, and designed to simultaneously hold the unit on the imaging medical device in a defined position.

19 Claims, 3 Drawing Sheets

(56) References Cited

U.S. PATENT DOCUMENTS

| | | | |
|---|---|---|---|
| 2008/0165282 A1* | 7/2008 | Marcy | F25D 23/028 348/552 |
| 2008/0200796 A1* | 8/2008 | Graham | G01R 33/28 600/411 |
| 2009/0043172 A1* | 2/2009 | Zagorchev | A61B 6/032 600/300 |
| 2010/0041332 A1* | 2/2010 | Flygh | G06F 1/1632 455/41.1 |
| 2010/0081377 A1* | 4/2010 | Chatterjee | G06F 1/1632 455/41.1 |
| 2010/0081473 A1* | 4/2010 | Chatterjee | G06F 1/1632 455/559 |
| 2010/0216397 A1* | 8/2010 | Takasu | G06F 1/1616 455/41.1 |
| 2011/0178384 A1 | 7/2011 | Kuth et al. | |
| 2012/0207273 A1 | 8/2012 | Kim et al. | |
| 2012/0278144 A1* | 11/2012 | Popilock | G06F 19/3406 705/14.4 |
| 2013/0088452 A1* | 4/2013 | Glaser-Seidnitzer | G06F 3/0488 345/173 |
| 2013/0123616 A1* | 5/2013 | Merritt | A61B 5/7445 600/427 |
| 2013/0197364 A1 | 8/2013 | Han | |
| 2013/0317753 A1* | 11/2013 | Kamen | G06F 19/3412 702/19 |
| 2014/0087788 A1* | 3/2014 | Filipovic | H04B 1/3888 455/557 |
| 2014/0121504 A1 | 5/2014 | Malchow et al. | |
| 2014/0188516 A1* | 7/2014 | Kamen | G06F 19/3406 705/3 |

FOREIGN PATENT DOCUMENTS

| | | |
|---|---|---|
| CN | 103034436 A | 4/2013 |
| DE | 10336276 A1 | 3/2005 |
| DE | 102005055048 A1 | 5/2007 |
| DE | 102010001092 A1 | 7/2011 |
| DE | 102011002426 A1 | 7/2012 |
| DE | 102011083957 A1 | 4/2013 |
| DE | 102012207114 A1 | 6/2013 |
| JP | 2004174019 A | 6/2004 |
| KR | 20090027722 A | 3/2009 |
| KR | 20120093590 A | 8/2012 |
| KR | 20130087291 A | 8/2013 |

OTHER PUBLICATIONS

Office Action for Korean Patent Application No. 10-2014-0180415 dated Jan. 13, 2016 and English translation thereof.
Office Action for Chinese Patent Application No. 201410785597.5 dated Jun. 23, 2017 and English translation thereof.

* cited by examiner

MEDICAL FACILITY

PRIORITY STATEMENT

The present application hereby claims priority under 35 U.S.C. §119 to German patent application number DE 102013226342.2 filed Dec. 18, 2013, the entire contents of which are hereby incorporated herein by reference.

FIELD

At least one embodiment of the invention generally relates to a medical facility, which includes an imaging medical device, by way of example a computer tomograph or a magnetic resonance tomograph, and an associated portable control and/or display unit, i.e. not permanently mechanically connected to the imaging medical device.

BACKGROUND

A medical facility is known by way of example from DE 10 2011 083 957 A1. Here an external touchscreen is connected to a medical device system via an interface.

A further medical facility is known for example from DE 10 2010 001 092 A1. In this case a medical imaging device can be controlled by means of a notebook, with data exchange being provided via Bluetooth.

DE 10 2011 002 426 A1 discloses a medical device with a central interface for interactions between a user and the device, it being possible to use different user control units to control the same medical device due to defined protocol structures such as RDP (Remote Desktop Protocol) or VNC (Virtual Network Computing Protocol).

SUMMARY

At least one embodiment of the invention is directed to a medical facility comprising at least one imaging device, paying particular regard to the control and maintenance effort, even in terms of hygiene.

At least one embodiment of the invention is directed to a medical facility including an imaging medical device and at least one portable control/display unit that cooperates therewith and enables wireless communication.

In an advantageous embodiment, the imaging medical device has a plurality of docking stations with different configurations, on which similar control/display units may be docked. The medical device is capable of recognizing docking of a control/display unit on a specific docking station and of transmitting configuration data to the control/display unit. The configuration data is specific data associated with the respective docking station.

BRIEF DESCRIPTION OF THE DRAWINGS

An example embodiment of the invention will be described below with reference to drawings, in which.

DETAILED DESCRIPTION OF THE EXAMPLE EMBODIMENTS

Figure 1:
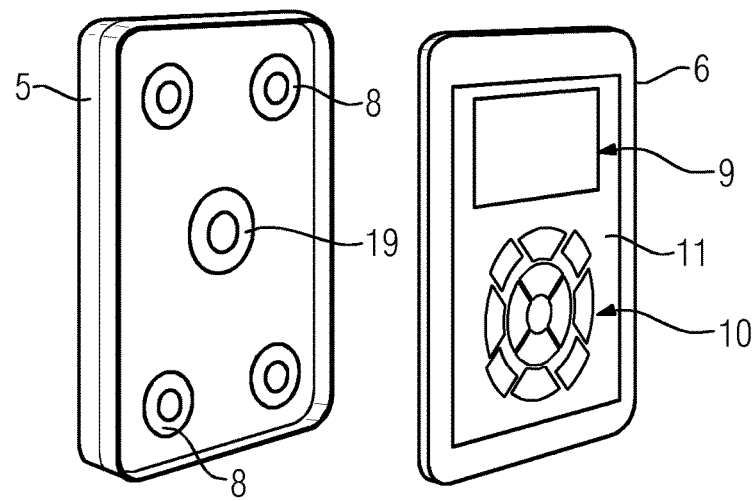
FIG. 1 shows a docking station and an associated control/display unit of an imaging medical device, namely a computer tomograph.
Figure 2:
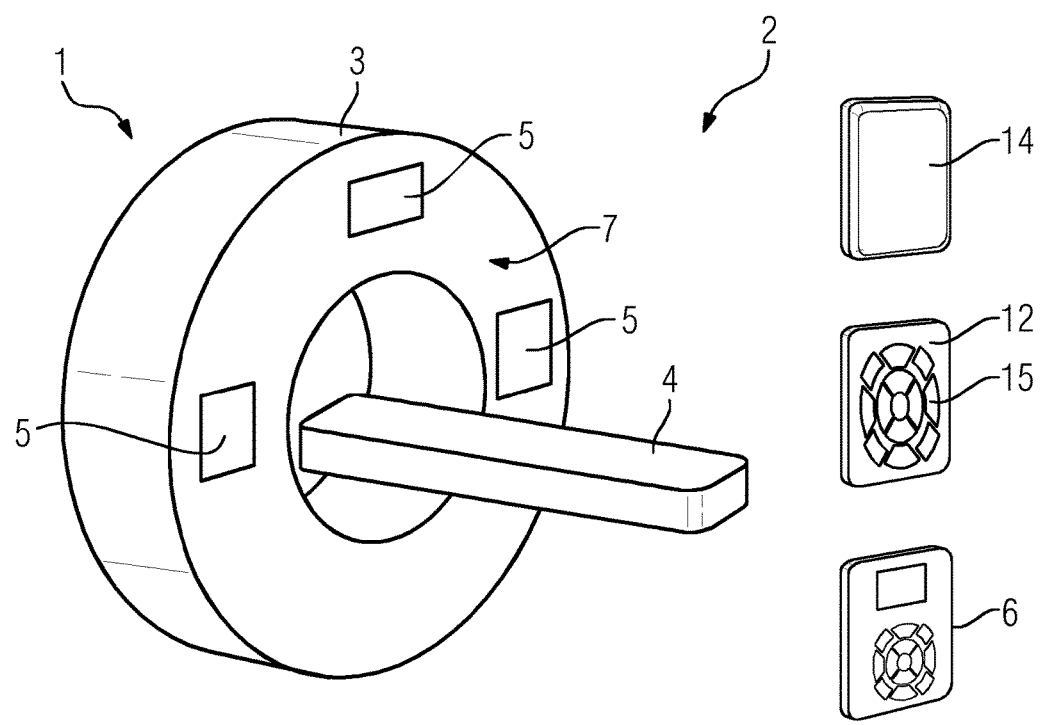
FIGS. 2-5 show in a schematic view one configuration respectively of a medical facility which comprises a computer tomograph as an imaging medical device and a control/display unit and further additional components.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An X-ray device, in particular a computer tomograph, or a magnet resonance device may be provided by way of example as an imaging medical device. There is at least one docking station, preferably a plurality of docking stations, located on the medical device, with each docking station being designed to establish a wireless data link to the control/display unit and to simultaneously fix the control/display unit in a defined position on the imaging medical device.

The fixing of the control/display unit on the docking station is configured in such a way that firstly the control/display unit cannot be detached from its defined position on the docking station due to loads, by way of example acceleration forces, that occur during designated operation of the medical facility and secondly, it can nevertheless be removed manually from the docking station without excessive expenditure of force. Magnetic retention of the control/display unit on the docking station is provided by way of example. Alternatively or additionally surface regions of the docking station and/or control/display unit may be resiliently yielding, with latching of the control/display unit on the docking station being provided.

In an embodiment that is particularly advantageous with respect to cleaning opportunities the surface of the docking station provided for attachment of the control/display unit is designed so as to be completely water-tight. The surface of the docking station can be formed by a component made of metal or plastics material here. In both cases the design of the surface of the docking station can be matched to the surface design of surrounding housing components of the medical device. A surface of the docking station and a surface region of the medical device surrounding the docking station are optionally formed by a shared covering.

Irrespective of whether the docking station is incorporated seamlessly into the surface of the medical device from the user's perspective or is visibly inserted as a separate component in a recess in the surface of the medical device, the docking station is preferably trough-shaped. This has the advantage firstly that it is particularly easy to see in which position the control/display unit should be attached to the docking station, and secondly represents effective protection against slippage of the control/display unit. It is not necessary to mechanically lock the control/display unit on the docking station therefore.

In an advantageous embodiment, the imaging medical device has a plurality of docking stations with different configurations, on which similar control/display units may be docked. The medical device is capable of recognizing docking of a control/display unit on a specific docking station and of transmitting configuration data to the control/display unit. The configuration data is specific data associated with the respective docking station.

In a standard setting of the medical facility, a first docking station can by way of example be provided for connection to a device that acts as a display unit. By contrast, a second docking station in the same medical facility can be provided by default for connecting a device with which it is possible to make entries for control of the medical device. Similar, universal control/display units can be docked at both docking stations. The automatic configuration performed by the medical device ensures that the functionality of the control/display unit as a display device is automatically activated in the event of a control/display unit being connected to the first docking station. On the other hand, the same control/display unit, as soon as it is connected to the second docking station, is automatically configured in such a way that it has the functionality of an input device.

With any configuration of a control/display unit, automatic monitoring of the data link between the docking station and the control/display unit is provided in a preferred embodiment. If a disruption, or complete break, to this data link is detected, by way of example to due removal of the control/display unit from the docking station or a disrupted power supply, then safety functions of the medical device can be triggered automatically. A safety function of this kind may include by way of example the performance or stoppage of certain motion sequences of the medical device.

In an advantageous embodiment in terms of safety the wireless data link between the control/display unit and docking station can be established only over the shortest distance, by way of example up to distances of a few centimeters or several tens of centimeters. An inductive coupling between the control/display unit and docking station can be provided in particular. Beyond a data link, charging of the control/display unit on the docking station can also be provided. Just like data transfer, charging also preferably takes place wirelessly, so there is no interruption in the smooth, easy-to-clean surface of the docking station due to a plug connection.

A plurality of uniformly designed docking stations of the medical device can be adapted for selective docking of an control/display unit, a pure input device, pure display unit, or a cover which does not have any kind of electrical functionality.

In an advantageous embodiment the control/display unit enabling data input and data display has a touch-sensitive surface. One possible construction and functionality of a touch-sensitive control unit having a large number of touch sensors is known in principle for medical devices by way of example from DE 10 2012 207 114 A1, the entire contents of which are hereby incorporated herein by reference.

An advantage of at least one embodiment of the invention lies in particular in that even safety-relevant functions of a medical device can be triggered by way of the mobile, standardized control/display unit due to the geometrically exactly defined coupling of a control/display unit to a docking station, linked with reliable, short-range, in particular inductive, data transfer. Functions of this kind are by way of example triggering of irradiation or the movement of a table of the medical device that is used for positioning a patient.

A computer tomograph 1 shown highly schematized in FIGS. 2 to 5 represents, as an imaging medical device, the main components of a medical facility designated as a whole by reference numeral 2. A gantry of the imaging medical device 1 is designated by reference numeral 3, an examination table by reference numeral 4. Reference is made to the prior art cited in the introduction with regard to the basic construction and function of the computer tomograph 1.

Three docking stations 5 are located on the gantry 3; one of these docking stations 5 is shown in an enlarged view in FIG. 1. Also shown in FIG. 1 is a control/display unit 6 which can also be seen in FIGS. 2,4,5. The control/display unit 6 is a device conventionally called a touch-panel.

Each docking station 5 is inserted in the substantially flat end face 7 of the gantry 3 and trough-shaped in design. A plurality of magnetic holding elements 8, which cooperate with holding elements (not visible in the Figures) on the back of the control/display unit 6, can be seen in FIG. 1 within the trough-shaped indentation which makes up virtually all of the visible surface of the docking station 5. In contrast to the design in FIG. 1, the visible surface of the docking station 5 may also be unstructured in design, without visible holding elements. At least one docking station 5 may also be located on the examination table 5 or another position of the medical facility 2 (not shown).

In the configuration according to FIGS. 1,2,4,5 the control/display unit 6 which can be attached to any docking station 5 in a respectively defined manner, either in portrait or landscape format, has a display panel 9 and an input panel 10. The two panels 9,10 of the control/display unit 6 are part of a continuous touch-sensitive surface 11 of the control/display unit 6.

As an alternative to the control/display unit 6, various other additional components 12,13,14 can be provided on each of the docking stations 5. In detail these are an input device 12 (FIGS. 2,4,5), a display unit 13 (FIGS. 3,4), and a cover 14 (FIGS. 2,3,4,5), which has no data processing function. The input device 12 and the display unit 13 are each provided solely for data input or data display respectively. The input device 12 is also called a gantry panel. In modified embodiments the input device 12 can also have a display function. The display unit 13 can analogously also have an input functionality whereby each of the devices 12,13 has an at least limited input functionality and at the same time an at least limited output functionality.

In the case of a development of the input device 12 without a supplementary function, in particular without a display function, individual buttons 15 of the input device 12 can be designed unchangeably as mechanically operable control elements. The function of the input device 12 is in this case unchangeable, irrespective of on which docking station 5 it is located.

The display unit 13 does not, unless it is also to be used for input purposes, necessarily have a touch-sensitive surface. Instead the surface of the display unit 13 can be a pure display surface in the sense of a screen. The functionality of the display unit 13 can be configurable here, with the configuration depending in particular on the selected docking station 5 on which the display unit 13 is provided.

Figure 3:
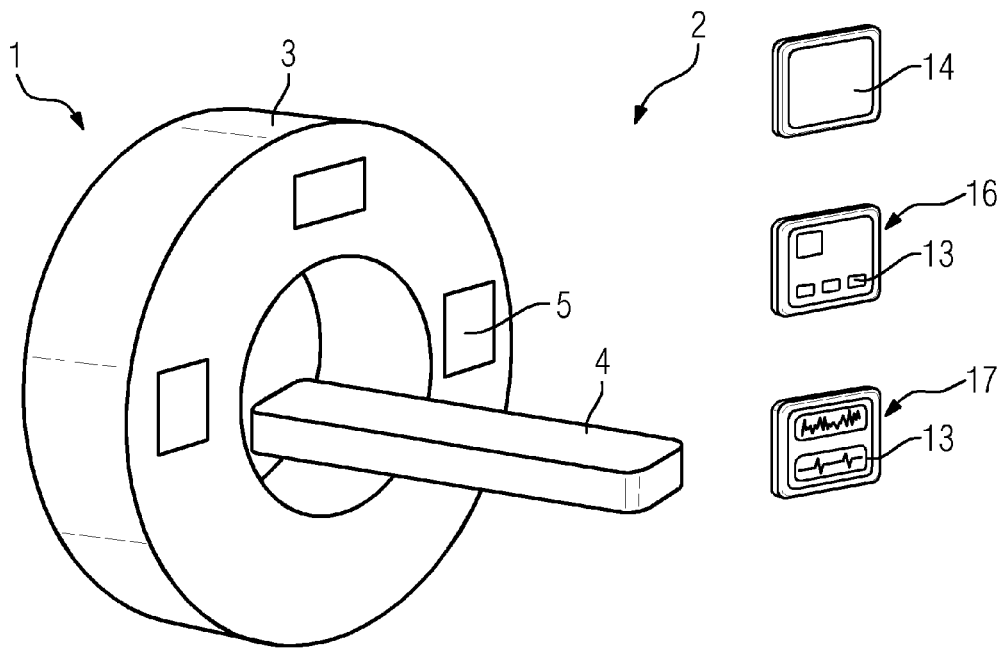
Figure 4:
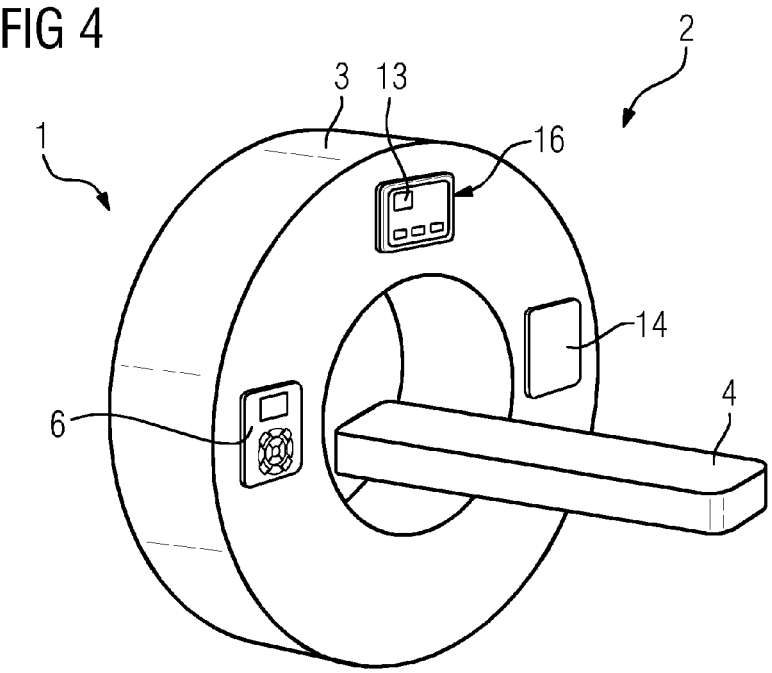
Figure 5:
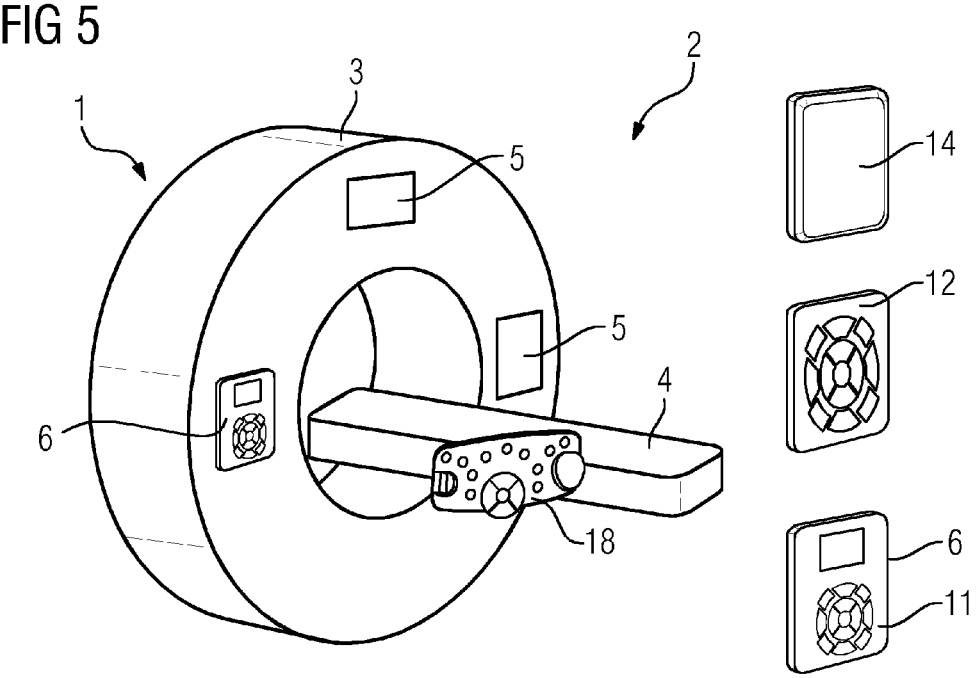

As indicated in the arrangements according to FIGS. 3 and 4, the display unit 13 can be used by way of example as an evaluation monitor 16. Data which can be processed for example by means of imaging software, which is marketed by the Applicants under the name Syngo.via®, can be displayed in this connection. It is also possible to use the display unit 13 as an ECG monitor 17 (FIG. 3).

Aside from the control/display unit 6, a keypad 18 may also be used, which may be spatially separate from the imaging medical device 1, for controlling the computer tomograph 1. One possible design of a keypad, which has a gap-free, sealed surface, is disclosed by way of example in DE 10 2005 055 048 A1, the entire contents of which are hereby incorporated herein by reference. In contrast to the arrangement according to FIG. 5, the keypad 18 may also be rigidly attached to a component of the imaging medical device 1 or to a different component of the medical facility 2.

Functions, which can be triggered by the keypad 18, can also be triggered by the control/display unit 6. However, in a preferred embodiment this applies only if the control/display unit 6 is located directly on a docking station 5, i.e. is docked on the computer tomograph 1 in a geometrically defined manner. A data link between the control/display unit 6 and the imaging medical device 1 can be established via a data transfer module 19, which works inductively and cooperates with a data transfer module (not visible in the Figures) inside the control/display unit 6. Charging of a battery in the control/display unit 6 is also possible by way of inductive coupling. The display unit 13 may also be supplied with electrical power in a corresponding manner. The same applies to the input device 12, if this is provided for connection to an external power supply.

The control/display unit 6 has the greatest functionality compared to display unit 13 and input device 12. Depending on which docking station 5 of the computer tomograph 1 or further component of the medical facility 2 the control/display unit 6 is docked on, this unit is automatically configured by way of example as a pure input device, pure display device, or, as shown in FIGS. 1,2,4,5, a combined input and display device. The automatic configuration of the control/display unit 6 can also be dependent on which docking station 5, and in what number further additional devices 12,13 is/are docked on the medical device 1.

Display functions by way of example can be completely or partially transmitted to the display unit 13 if this, as shown in FIG. 4, is docked on the medical device 1. If this is not the case, the corresponding display function is assumed by the control/display unit 6. Overall, the functions, which are provided by the control/display unit 6, input device 12, and display unit 13, can therefore be used extremely flexibly, with individual functionalities automatically being spread among the control/display unit 6 and/or the respectively suitable additional components 12,13.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A medical facility, comprising:
an imaging medical device including a plurality of docking stations each docking station formed as a recess in an exterior surface of the imaging medical device; and
at least one portable control/display unit fitted into a docking station, each of the docking stations including a surface having a data connection designed to establish a wireless data link to the control/display unit and a fixing connection to simultaneously hold the control/display unit on the imaging medical device in a defined position, wherein
a control/display unit is insertable into the docking station, and wherein the docking stations are of different configurations, and the imaging medical device is configured to recognize docking of a control/display unit in a specific docking station and to transmit configuration data to the docked control/display unit based on the respective docking station to which the control/display unit is docked, the configuration data being specific data associated with the respective docking station to control functionality of the imaging medical device.

2. The medical facility of claim 1, wherein the at least one portable control/display unit is magnetically fixable to one of the docking stations.

3. The medical facility of claim 1, wherein at least one of the docking stations includes a completely water-tight surface.

4. The medical facility of claim 1, wherein the imaging medical device is designed to monitor a data link between at least one of the docking stations and the at least one portable control/display unit.

5. The medical facility of claim 1, wherein the at least one portable control/display unit and at least one of the docking stations is designed for inductive data transfer.

6. The medical facility of claim 1, wherein the at least one portable control/display unit includes a touch-sensitive surface.

7. The medical facility of claim 1, wherein the docking stations are each designed for selective docking of a control/display unit, an input device, a display device, and cover that that blocks access to the docking station.

8. The medical facility of claim 1, wherein at least one of the docking stations is designed for wireless charging of the at least one portable docked control/display unit.

9. The medical facility of claim 1, wherein a computer tomograph is provided as the imaging medical device.

10. The medical facility of claim 2, wherein the imaging medical device is designed to monitor a data link between at least one of the docking stations and the at least one portable control/display unit.

11. The medical facility of claim 2, wherein the at least one portable control/display unit and at least one of the docking stations is designed for inductive data transfer.

12. The medical facility of claim 2, wherein the at least one portable control/display unit includes a touch-sensitive surface.

13. The medical facility of claim 2, wherein the docking stations are each designed for selective docking of an control/display unit, an input device, a display device, and a cover that blocks access to the docking station.

14. The medical facility of claim 2, wherein at least one of the docking stations is designed for wireless charging of the docked control/display unit.

15. The medical facility of claim 2, wherein a computer tomograph is provided as the imaging medical device.

16. The medical facility of claim 3, wherein the docking stations include different configurations, designed to configure a docked control/display unit in a specific way based on the respective docking station.

17. The medical facility of claim 3, wherein the imaging medical device is designed to monitor a data link between at least one of the docking stations and the at least one portable control/display unit.

18. The medical facility of claim 1, wherein docking stations are automatically configured by the imaging medical device such that the functionality of a control/display unit in a first docking station is of a display device and the functionality of a same control/display unit in a second docking station is of an input device.

19. The medical facility of claim 1, wherein surface regions of at least one of the docking stations or the control/display units is resiliently yielding, with latching of the control/display unit on the docking station being provided.

* * * * *